United States Patent [19]

Yoshimura et al.

[11] Patent Number: 5,077,397
[45] Date of Patent: Dec. 31, 1991

[54] SIALIC ACID DERIVATIVE WITH ACTIVE ESTER GROUPS

[75] Inventors: Shoji Yoshimura, Iruma; Makoto Tanaka, Koshigaya, both of Japan

[73] Assignee: MECT Corporation, Tokyo, Japan

[21] Appl. No.: 441,270

[22] Filed: Nov. 27, 1989

[30] Foreign Application Priority Data

Nov. 29, 1988 [JP] Japan .................. 63-301955

[51] Int. Cl.$^5$ .................. C07H 5/06; C07H 15/20
[52] U.S. Cl. .................. 536/53; 536/4.1; 536/17.2; 536/17.5; 536/119
[58] Field of Search .................. 536/53, 4.1, 17.2, 17.5, 536/119; 514/23, 24, 25, 35

[56] References Cited

U.S. PATENT DOCUMENTS

| | | | |
|---|---|---|---|
| 4,914,035 | 4/1990 | Hasegawa et al. | 536/18.6 |
| 4,918,177 | 4/1990 | Yoshimura et al. | 536/18.7 |
| 4,963,653 | 10/1990 | Nagai et al. | 530/322 |

FOREIGN PATENT DOCUMENTS

2101588 1/1983 United Kingdom .................. 536/53

OTHER PUBLICATIONS

Privalova et al.; Izv. Akad. Nauk SSSR, Ser. Khim. 12:2785-2792 (1969).

Shimizu et al.; Carbohydrate Research, 166:314-316 (1987).

*Primary Examiner*—Ronald W. Griffin
*Assistant Examiner*—Nancy S. Carson
*Attorney, Agent, or Firm*—Rodman & Rodman

[57] ABSTRACT

Sialic acid derivative with active ester groups expressed with the formula [I]

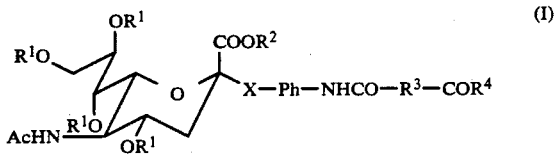

Where $R^1$ denotes hydrogen or an acetyl group, $R^2$ denotes hydrogen or a lower alkyl group, $R^3$ denotes $C_2H_4$, $C_3H_6$ or $C_2H_2$, $R^4$ denotes an hydroxyl group, the residue left after removing hydrogen from the alcohol portion of the active ester or alkyloxycarbonyloxy group, AC denotes an acetyl group, Ph denotes an phenyl group, and X denotes oxygen or sulfur. This sialic acid derivative has high reactivity because it has active ester groups in the molecules and can be used as a raw material or intermediate for synthesis of various sialic acid derivatives.

18 Claims, No Drawings

SIALIC ACID DERIVATIVE WITH ACTIVE ESTER GROUPS

BACKGROUND OF THE INVENTION

1. Field of the Invention

This invention relates to new sialic acid derivatives and more specifically to sialic acid derivatives having active ester groups in the molecules, biochemical half life extenders of biologically active substances, sialic acid derivatives bonding these sialic acid derivatives with amino compounds, and intermediate compounds used for synthesis of the sialic acid derivatives.

2. Related Art Statement

Neuraminic acid derivatives including N-acetylneuraminic acid, that is, sialic acid derivatives, are known to exist widely in the animal world or on the cell surface of several bacteria such as sialo complexes, more specifically, glycoproteins, glycolipids, oligosaccharides, and polysaccharides.

The above-mentioned sialic acid derivatives are compounds which have recently become highly valuable in medical and pharmaceutical fields, in the treatment of nervous functions, cancer, inflammation, immunity, virus infection, differentiation, and hormone receptor, and are attractng keen attention as particularly active molecules located on the cell surface.

Various theories have been set forth about the role played by sialic acid derivatives in the aforementioned sialo complex, but there are many things that have not yet been clarified, and are still a matter of conjecture.

The inventors have studied sialic acid derivatives for many years and succeeded in synthesizing sialic acid derivatives which exhibit conspicuous biological activity (Japanese Patent Application No.62-295641).

Recently, the inventors discovered a new sialic acid derivative that exhibits conspicuous biological activity and in the subject matter of this invention.

SUMMARY OF THE INVENTION

Therefore, an object of the present invention is to provide a new sialic acid derivative which exhibits high reactivity with various amino compounds.

Another object of the present invention is to provide biological half-life extenders of various biologically active substances using the said sialic acid derivative.

Still another object of the present invention is to provide a new sialic acid derivative which bonds the said sialic acid derivative to various amino compounds including amino acids and amines through amide bonding.

A further object of the present invention is to provide a new sialic acid derivative which is useful as the intermediate for synthesis of the inventive sialic acid derivative.

The above and other objects, features, and advantages of the present invention will become more apparent from the following detailed description and embodiments.

The sialic acid derivative of the present invention has active ester groups expressed by the formula [I].

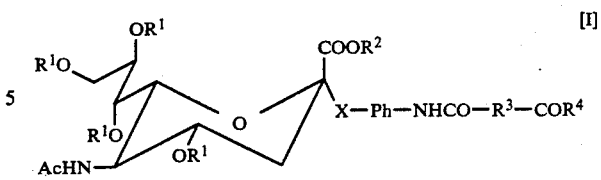

where $R^1$ denotes hydrogen or an acetyl group, $R^2$ denote hydrogen or a lower alkyl group, $R^3$ $C_2H_4$, $C_3H_6$ or $C_2H_2$, $R^4$ denotes an hydroxyl group, the residue left after removing hydrogen from the alcohol portion of an active ester or alkyloxycarbonyloxy group, Ac denotes an acetyl group, Ph denotes a phenyl group, and X denotes oxygen or sulfur.

In the said sialic acid derivative, the residue $R^4$ left after removing hydrogen from the alcohol portion of the active ester includes N-hydroxysuccinimide, N-hydroxy-5-norbornene-2, 3-dicarboximide, N-hydroxyphthalimide, N-hydroxybenzotriazole, p-nitrophenol, 2, 4-dinitrophenol, 2, 4, 5trichlorophenol, or pentachlorophenol. r The alkyloxycarbonyloxy group ($R^4$) is introduced by allowing carboxylic acid to react with alkyl or aryl halogenoformates in the presence of bases, wherein the alkyl group includes methyl group, ethyl group, n butyl group, isobutyl group, and the aryl group includes the phenyl group, and benzyl group.

The sialic acid derivative containing the ester group is prepared by the following method using N-acetyl neuraminic acid having the following formula as starting material.

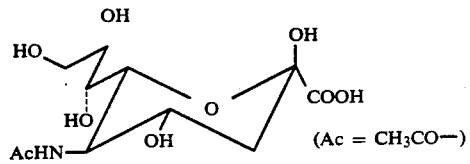

(Ac = $CH_3CO-$)

where Ac denotes a acetyl group. The same applies to the following.

At first, the methyl ester substance is produced at a high yield by letting N-acetylneuraminic acid react with methanol in the presence of an ion-exchange resin Dowex 50 w (H+). Then, the methyl-ester compound is allowed to react with excess acetyl chloride ($CH_3COCl$), then with ethanol while cooling, to give the chlor substance at a high yield. Then, this chlor substance is allowed to react with anhydrous sodium salt of p nitrophenol in the anhydrous dimethylformamide to give p-nitrophenylglycoside at a high yield. The p-nitrophenylglycoside is a known compound described in "Carbohydrate Research, 162 (1987) 294–297" and details of the synthesis method will be discussed in Embodiment 1 herein.

The chlor substance is allowed to react with anhydrous sodium salt of p-nitrothiophenol in the anhydrous dimethylformamide to give p-nitrophenylthioglycoside (Embodiment 2). Then, to the aforementioned p-nitrophenylglycoside, hydrogen is added in the presence of 5% Pd/C in the methanol to give p-aminophenylglycoside (Embodiment 3). Adding hydrogen to the p-nitrophenylthioglycoside in the presence of 5% Pd/C in methanol expedites the reductive alkylation reaction and N, N'-dimethylaminophenyl-thioglycoside is obtained (Embodiment 4). On the other hand, adding hydrogen to the p-nitrophenylthioglycoside in the acetic acid in the presence of 5% Pd/C give p-aminophenylthioglycoside (Embodiment 5). Next, the said p-aminophenylglycoside is allowed to react with slightly excess succinic anhydride in anhydrous tetrahydrofuran to give an amido-carboxylic acid compound (Embodiment 6). The p-aminophenylthioglycoside is allowed to react with slightly excess succinic anhydride in anhydrous tetrahydrofuran to give an amido carboxylic acid compound (Embodiment 8). Alternatively, the above mentioned p-aminophenylglycoside is allowed to react with maleic anhydride in anhydrous tetrahydrofuran to give an unsaturated amido carboxylic acid compound (Embodiment 7). Next, the amido carboxylic acid compound is allowed to react with sodium methoxide in anhydrous methanol, and is then neutralized by Dowex 50 w (H+) to give deacetylated substance (Embodiment 9).

Because the sialic acid derivatives of this invention shown by the aforementioned formula [I] contain the active ester group, they exhibit high reactivity to other compounds containing functional groups that can react with ester groups, such as amino compounds. The sialic acid derivative of this invention containing active ester groups is an extremely useful compound as a raw material or intermediate to synthesize various sialic acid derivatives.

Another sialic acid derivative of this invention has the formula [II] as follows:

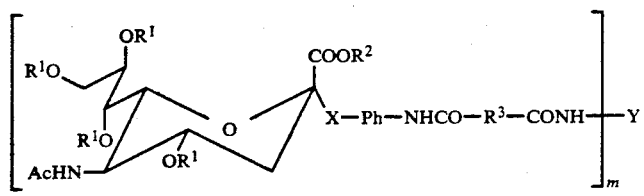

where $R^1$ is hydrogen or an acetyl group, $R^2$ hydrogen or a lower alkyl group, $R^3$ is selected from $C_2H_4$, $C_3H_6$ or $C_2H_2$, Ac is a acetyl group, m is 1–60, Ph phenyl group, X is oxygen or sulfur, and Y is the residue left from removing m number of amino groups from amino compounds. The amino compounds include amine of lower class and amino acids.

The sialic acid derivative can be prepared from amino compounds and sialic acid derivatives containing the aforementioned active ester group by the use of the active ester process and the mixed acid anhydride process.

The active ester process produces N-oxysuccinimide ester mixing the amido-carboxylic acid compound with DSC (N, N'-disuccinimidyl carbonate) in anhydrous acetonitrile (Embodiment 10). In this reaction, adding anhydrous pyridine at more than an equivalent mole ratio causes the N-oxysuccinimide ester to transfer to the p-succinimidophenylglycoside of intramolecular ring closure (Embodiment 11). The amido carboxylic acid compound is allowed to react in anhydrous tetrahydrofuran in the presence of WSC (1 ethyl-3-(3-dimethylaminopropyl)-carbodiimide) the condensing agent to give the p-nitrophenyl ester (Embodiment 12). The said ester is not isolated and is allowed to react by adding amino acid methyl ester in the solution to give an amide, the sialic acid derivative of this invention (Embodiment 13-1).

Alternatively, in the mixed acid anhydride process, the amido-carboxylic compound is allowed to react with isobutylchloroformate in anhydrous tetrahydrofuran to give a mixed acid anhydride, Then, the mixed acid anhydride is allowed to react with amino acid methyl ester to give the amide of this invention (Embodiment 13-2). Incidentally, the use of this mixed acid anhydride process can produce the amide from the deacetyl of the amido carboxylic acid compounds under similar reaction conditions (Embodiment 15).

For other processes, there is a method to produce a peracetylated substance by allowing the amide to react with acetic anhydride in anhydrous pyridine (Embodiment 13-3). As reaction species other than the amino acid ester, hydrazine is allowed to react with the N-hydroxysuccinimide ester isolated or in solution in anhydrous acetonitrile to give an acid hydrazide (Embodiment 14).

The sialic acid derivatives of this invention having the aforementioned formula [II] are compounds consisting of sialic acid derivatives represented by the aforementioned formula [I] and amino compounds. For example, when an amino acid is administered to animals or human bodies as nutrient, or when insulin, growth hormone, interferon, and immunogen are administered as medicine, it is predicted that administration of these medicines as the sialic acid derivative of formula [II] will prevent or delay biological reactions of a biologically active substance by the presence of sialic acid. This will produce the beneficial effects of increasing the durability of biologically active substances in the body or displaying desired medicinal effects with a small amount of administration. The sialic acid derivative represented by the said formula [I] is an extremely useful compound as an extender of the biological half-life of various biologically active substances.

DETAILED DESCRIPTION OF THE PREFERRED EMBODIMENTS

In the examples, embodiments of the sialic acid derivative according to the present invention will now be described in detail. However, the present invention is not limited by these embodiments.

[Embodiment 1]

Synthesis of methyl (4-nitrophenyl 5-acetamido 4, 7, 8, 9-tetra-O-acetyl-3, 5-dideoxy-α-D-glycero D galacto-2-nonulopyranosido)onate (1) N-acetylneuraminic acid was allowed to react in methanol in the presence of Dowex 50 w (H+) at the room temperature for six hours to give methyl ester substance (yield=80%).

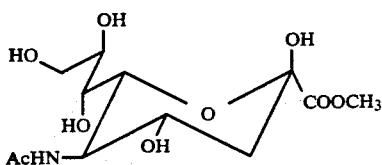

(2) After the methyl ester was allowed to react with excess acetyl chloride for one day, ethanol was added with cooling (−30° C.), and it was allowed to stand for 10 days to give the following chlor substance (yield=83%).

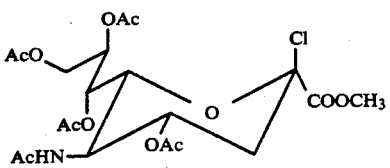

(3) 10.26 g of the anhydrous sodium salt of p-nitrophenol and 6.0 g of the chlor substance obtained in Step 2 (methyl 5-acetamide 4, 7, 8, 9-tetra-O-acetyl-2 chloro-3,5 dideoxy-α-D-glycero-D-galacto-nonulopyranosonate) were dissolved in 120 ml of anhydrous dimethylformamide, and were allowed to react with stirring for 24 hours under moisture-proof conditions.

Then, the solvent was removed from the solution under reduced pressure, xylene was added, and solvent was repeatedly removed. Ethyl acetate was added to the residue obtained and stirred, and the residue was extracted thoroughly with ethyl acetate. The solvent was removed from the extract liquid and the residue was purified with silica gel column chromatography (Wakogel C-300). At first, p-nitrophenol was eluted from the residue with ether, and after removal, it was eluted with ethyl acetate to give a fractional solution containing the object. The solvent was removed from the fractional solution and an oily substance (crude yield point=6.87 g, crude yield=95.4%, melting point=95°-98° C.) was obtained.

TLC: Rf=0.41 (Kieselgel 60 F$_{254}$, Merck product, acetate)

Rf=0.44 (Kieselgel 60 F$_{254}$, Merck product, CHCl$_3$MeOH=20/1)

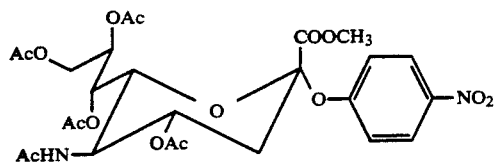

Reference (1) In Volker Eschenfelder and Reinhard Brossmer, Carbohydrate Research 162 (1987) 294–297, the aforementioned synthesis method is described, but the yield is as poor as 57% (melting point=104°-108° (dec.) (ether/hexane).

Physical Properties of the product $^1$H-N (CDCl$_3$, TMS)
1 932 (3H, s, —NHCOCH$_3$),
2.055;2.061;2.119;2.193 (all 3H, all s, —OCOCH$_3$ X 4),
2.304 (1H, t, J=12.8 Hz, H$_{3ax}$),
2.744 (1H, dd, J=13.2 Hz, 4.8 Hz, H$_{3eq}$),
3.663 (3H, s, 2'COOCH$_3$),
4.986 (1H, ddd, J=12.1, 10.3, 4.8 Hz, H-4),
7.153 (2H, d, J=9.2 Hz, phenyl-H)
8.189 (2H, d, J=9.2 Hz, phenyl-H).
IRνKBr/maxcm$^{-1}$: 1740, 1660, 1520, 1340, 1220,

Embodiment 2

Synthesis of methyl (4-nitrophenyl 5-acetamido-4, 7, 8, 9 tetra-O-acetyl-2, 3, 5-trideoxy-2-thio-α-D-glycero-D-galacto-2-nonulopyranosido)onate:

The anhydrous sodium salt of p-nitrothiophenol was prepared from 19.6 ml of methanol solution of 1.67 g of p-nitrothiophenol, 0.5 mol of sodium methoxide, and 1.0 g of the chlor substance obtained in Embodiment 1 (2) (methyl 5-acetamide-4, 7, 8, 9 tetra-O-acetyl-2-chloro-3, 5-dideoxy-β-D-glycero-D-galacto-1-nonulopyranosonate) was dissolved in 15 ml of anhydrous dimethylformamide and allowed to react with stirring for 6 hours at room temperature under moisture-proof conditions and a nitrogen atmosphere. Then, after solvent was removed under reduced pressure, xylene was added and solvent was repeatedly removed. The residue obtained was purified with silica gel column chromatography (Wakogel C-300, ethyl acetate) twice and solvent was again removed from the fractional solution, and finally 0.52 g white powder was obtained (yield=42.4%, melting point=94°-96° C.).

TLC: Rf=0.44 (Kieselgel 60 F$_{254}$, Merck product, ethyl acetate)

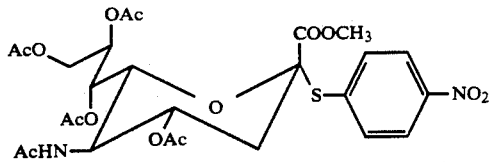

Physical properties of the product

C$_{26}$H$_{32}$O$_{14}$N$_2$S
FAB-MS m/z : 629 (M$^+$+1)
$^1$H-NMR ppm/500 MHz (CDCl$_3$, TMS)
1.891 (3H, s, —NHCOCH$_3$), 2.041;2.061;2.063;2.165 (all 3H, all s,—OCOCH$_3$ X 4), 2.869 (1H, dd, J=12.8, 4.8 Hz, H$_{3eq}$),
3.611 (3H, s, 2-COOCH$_3$),
4.883 (1H, ddd, J=12.1, 10.3, 4.8 Hz, H-4),
7.655 (2H, d, J=8.8 Hz, phenyl-H),
8.192 (2H, d, J=8.8 Hz, phenyl-H).
IRνKBr/max cm$^{-1}$: 3250, 1750, 1650, 1550, 1520, 1350,

Embodiment 3

Synthesis of methyl (4-aminophenyl 5 acetamido 4, 7, 8, 9-tetra-0-acetyl-3, 5-dideoxy-α-D-glycero-D galacto-2-nonulopyranosido)onate: V 6 87 g of methyl (4-nitrophenyl 5-acetamido-4,7,8, 9-tetra-O-acetyl-3, 5-dideoxy-α-D-glycero-D-galacto-2-nonulopyranosido)onate) obtained in the aforementioned Embodiment 1 (3) were dissolved in 50 ml of methanol. After a slight amount of 5% palladium/carbon was added with a spatula, it was reduced with hydrogen with stirring at room temperature. Then after allowing reaction to proceed for 2 days, the reagents were removed by filtering. Solvent was removed from the filtrate and 4.91 g of an oily substance (yield=71.63%) was obtained. It was further purified by the use of silica gel column chromatography (Wakogel C-300, CHCl₃/MeOH=40/1) and white powdery crystals (melting point: 95°–99 ° C.) was obtained as TLC one spot purified product as shown below.

TLC: Rf=0.29 (Kieselgel 60 F$_{254}$, Merck product, ethyl acetate)

Rf=0.35 (Kieselgel 60 F$_{254}$, Merck product, CHCl₁₃/MeOH=20/1)

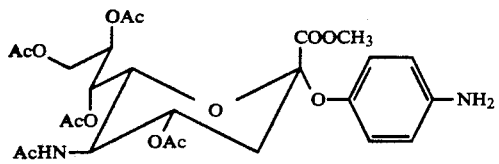

Physical properties of the product $C_{26}H_{34}O_{13}N_2$
FAB-MS m/z : 583 (M⁺ + 1)
¹H-NMR pp/m500 MHz (CDCl₃, TMS)
1.896 (3H, s, —NHCOCH₃),
2.028;2.055;2.115;2.139 (all 3H, all s,—OCOCH₃ X 4),
2.676 (1H, dd, J=12.8, 4.8 Hz, H₃eq),
3.671 (3H, s, 2-COOCH₃),
4.936 (1H, J=12.1, 10.3, 4.8 Hz, H-4),
6.569 (2H, d, J=8.8 Hz, phenyl-H),
6.886 (2H, d, J=8.8 Hz, phenyl-H).
IRνKBr/max cm⁻¹: 3450, 3370, 1740, 1660, 1540,

Embodiment 4

Synthesis of methyl (4-dimethylaminophenyl 5-acetamido-4, 7, 8, 9-tetra-O-acetyl-2, 3, 5-trideoxy-2-thio-α-D-glycero-D-galacto-2-nonulopyranosido)onate:

0.25 g of [methyl (4-nitrophenyl 5 acetamido-4, 7, 8, 9-tetra-0-acetyl-2, 3, 5-trideoxy-2-thio-α-D glycero-D galacto-2-nonulopyranoside)onate) obtained in the aforementioned Embodiment 2 were dissolved in 10 ml of methanol. After a slight amount of 5% palladium/-carbon was added with a spatula, it was reduced with hydrogen with stirring at room temperature for one day. Then reagents were removed by filtering. The solvent was removed from the filtrate and the residue was purified with silica gel column chromatography (Wakogel C-300, CHCl₃/MeOH=40/1). Solvent was removed from the fractional solution containing the product and 100 mg of white powdery crystals were obtained (yield=40%, melting point=83°–85 ° C.).

TLC: Rf=0.50 (Kieselgel 60 F$_{254}$, Merck product, chloroform/methanol=20/1)

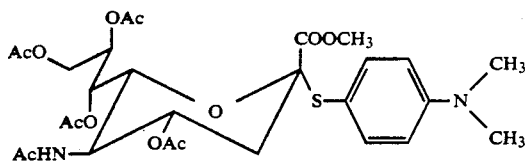

Physical properties of the product $C_{28}H_{38}O_{12}N_2S$
FAB-MS m/z : 627 (M⁺ + 1)
¹H-NMR ppm/500 MHz (CDCl₃, TMS)
1.853 (3H, s, —NHCOCH₃),
1.970 (1H, t, J=12.8 Hz, H₃ax),
2.011;2.054;2.133 (3H;6H;3H, all s, —OCOCH₃ X 4),
2.742 (1H, dd, J=12.8, 4.8 Hz, H₃eq),
2.987 (6H, s,

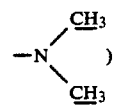

3.636 (3H, s, 2 COOCH₃),
4.829 (1H, ddd, J=11.7, 10.3, 4.8 Hz, H-4),
6.614 (2H, d, J=8.8 Hz, phenyl-H),
7.330 (2H, d, J=8.8 Hz, phenyl-H).
IRνKBr/max cm⁻¹: 3360, 1740,

Embodiment 5

Synthesis of methyl (4-aminophenyl 5 acetamido-4, 7, 8, 9-tetra-0-acetyl-2, 3, 5-trideoxy-2-thio-α-D-glycero D galacto-2-nonulopyranosido)onate:

0.10 g of methyl (4-nitrophenyl 5-acetamido-4, 7, 8, 9-tetra-0-acetyl-2, 3, 5-trideoxy-2 thio-α-D-glycero-D galacto-2-nonulopyranosido)onate) obtained in the aforementioned Embodiment 2 were dissolved in 5 ml of acetic acid. After a slight amount of 5% palladium/-carbon was added with a spatula, it was reduced with hydrogen with stirring at room temperature. Then reagents were removed by filtering. Solvent was removed from the filtrate and the residue was purified with silica gel column chromatography (Wakogel C-300, CHCl₃/MeOH=40/1). Therein, the solution of the residue was neutralized with triethylamine, then developed. Solvent was removed from the fractional solvent containing the product and 67 mg of white powdery crystals were obtained (yield=70%, melting point=100°14 102 ° C.).

TLC: Rf=0.29 (Kieselgel 60 F$_{254}$, Merck product, chloroform/methanol=20/1)

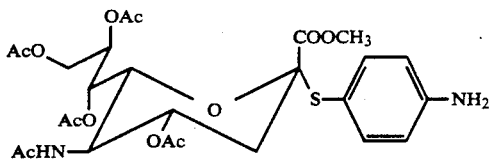

Physical properties of the product $C_{26}H_{34}O_{12}N_2S$
FAB-MS m/z : 599 (M⁺ + 1)
1H-NMR ppm/500 MHz (CDCl₃, TMS)
1.858 (3H, s, —NHCOCH₃),
1.978 (1H, t, J=12.5 Hz, H₃ax),
2.016;2.054;2.060 2.138 (all 3H, all s, —OCOCH₃ X 4),
4.144 (1H, dd, J=12.8, 4.8 Hz, H₃eq),
3.618 (3H, s, 2 COOCH₃),
603 (1H, d, J=8.8 Hz, phenyl-H),
266 (1H, d, J=8.8 Hz, phenyl-H),
IRνKBr/max cm⁻¹ 3470, 3380, 1740,

Embodiment 6

Synthesis of 4'-[(methyl 5-acetamido 4, 7, 8, 9-tetra-0-acetyl-3, 5-dideoxy-α-D glycero-D-galacto-2-nonylopyranosylonate) oxy] succinanilic acid:

4.91 g of [methyl (4-aminophenyl 5-acetamido-4, 7, 8, 9-tetra-0-acetyl-3, 5-dideoxy-α-D-glycero-D-galacto-2-nonulopyranosido)onate] obtained in the aforementioned Embodiment 3 and 1.26 g of succinic anhydride were dissolved in 100 ml of anhydrous tetrahydrofuran and allowed to react for one day with stirring at room temperature. After the disappearance of raw materials was confirmed with a TLC, reaction solvent was removed under reduced pressure and the residue was purified with gel filtration chromatography (LH-20, MeOH) and the fractional solution not containing succinic anhydride was obtained. The residue obtained by removing solvent from the fractional solution was recrystallized with acetate, and 4.81 g of the product was obtained (total up to the third crystal, yield=83.7%, melting point=130°-131 ° C.).

TLC Rf=0.13 (Kieselgel 60 $F_{254}$, Merck product, CHCl$_3$/MeOH=20/1)

Rf=0.42 (Kieselgel 60 $F_{254}$, Merck product, CHCl$_3$/MeOH=10/3)

were dissolved in 3 ml of anhydrous tetrahydrofuran and stirred at room temperature. The reactions took place immediately. After the disappearance of raw materials was confirmed with a TLC, reaction solvent was removed under reduced prsesure. The residue was purified with gel filtration chromatography (LH-20, MeOH) and the fractional solution containing the product was obtained. From this fractional solution, solvent was removed and 74.8 mg of pale yellow powdery crystals were obtained (yield=67.4% melting point=121°-123° C.).

TLC: Rf=0.33 (Kieselgel 60 $F_{254}$, Merck product, CHCl$_3$/MeO=10/3)

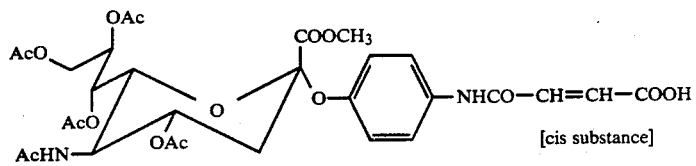

[cis substance]

Physical properties of the product $C_{30}H_{36}O_{16}N_2$
FAB-MS m/z: 681 ($M_++1$)
$^1$H-NMR ppm/500 MHz (CDCl$_3$, TMS)
1.929 (3H, s, NHCOCH$_3$),
2.047;2.095;2.140 2.145 (all 3H, all s, —OCOCH$_3$ X
2.243 (1H, t, J=12.8 Hz, H$_{3ax}$),
2.715 (1H, dd, J=12.8, 4.4 Hz, H$_{3eq}$),
3.654 (3H, s, 2—COOCH$_3$),
4.955 (1H, ddd, J=12.1, 10.6, 4.4 Hz, H 4),
6.455 (1H, d, J=12.8 Hz, olefin H),

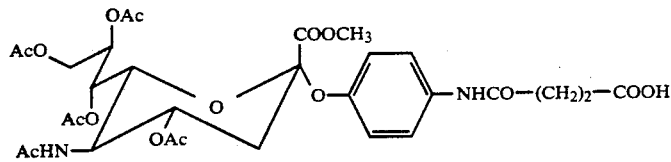

Physical properties of the product $C_{30}H_{38}O_{16}N_2$
FAB-MS m/z : 683 ($M^++1$)
H-NMR ppm/500 MHz (CDCl$_3$, TMS)
1.890 (3H, s, —NHCOCH$_3$),
2.041;2.051;2.121 2.126 (all 3H, all s, —OCOCH$_3$ X 4),
2.186 (1H, t, J=12.5 Hz, H$_{3ax}$),
2.655-2.710 (3H, m, —CH$_2$CH$_2$-+H$_{3eq}$)),
2.777 (3H, t, J=6.6 Hz, —CH$_2$CH$_2$—),
3.643 (3H, s, -COOCH$_3$),
4.964 (2H, ddd, J=12.1, 10.3, 4.8 Hz, H-4),
7.011 (2H, d, J=9.2 Hz, phenyl-H),
7.418 (2H, d, J=9.2 Hz, phenyl-H).
IR$\nu$KBR/max cm$^{-1}$ 3350, 1740, 1660, 1540,

Embodiment 7

Synthesis of 4'-[(methyl (5-acetamido 4,7,8,9-tetra-O-acetyl-3, 5-dideoxy-α-D-glycero-D-galacto-2-nonulopyranosylonate)oxy] maleanilic acid 100 g of [methyl (4 aminophenyl 5-acetamido-4, 7, 8, 9-tetra-0-acetyl-3, 5 dideoxy-α-D-glycero-D-galacto-2 nonulopyranosido)onate] obtained in the aforementioned Embodiment 3 and 24 mg of maleic anhydride 6.499 (1H, d, J=12.8 Hz, olefin H),
7.048 (2H, d, J=8.8 Hz, phenyl-H),
7.543 (2H, d, J=8.8 Hz, phenyl-H),
IR$\nu$KBr/max cm$^{-1}$ 3350, 1750, 1770, 1550,

Embodiment 8

Synthesis of 4'-[methyl (5-acetamido 4, 7, 8, 9-tetra-O-acetyl-3, 5-dideoxy-α-D-glycero-D-galacto-2-nonulopyranosylonate) thio] succinanilic acid 0.1 g of [methyl (4 aminophenyl 5-acetamide-4, 7, 8, -tetra-0-acetyl 3, 5 dideoxy-α-D-glycero D galacto-2 nonulopyranosido)onate] obtained in the aforementioned Embodiment 5 and 20 mg of succinic anhydride were dissolved in 3 ml of anhydrous tetrahydrofuran and were allowed to react with stirring for one day at room temperature. After the disappearance of raw materials was confirmed with a TLC, reaction solvent was removed under reduced pressure conditions. The residue was purified with gel filtration chromatography (LH-20, MeOH) and a fractional solution containing the product was obtained. From this fractional solution, solvent was removed and 9.4 mg of white powdery crystals were obtained (yield=82%, melting point=119°-121 ° C.).

TLC: Rf=0.40 (Kieselgel 60 F$_{254}$, Merck product, CHCl$_3$/MeOH=10/3)

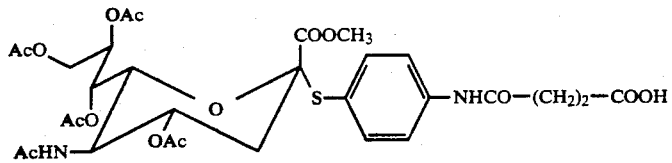

Physical properties of the product

TLC: Rf=0.40 (Kieselgel 60 F$_{254}$, Merck product, CHCl$_3$/MeOH=6/3/0.5)

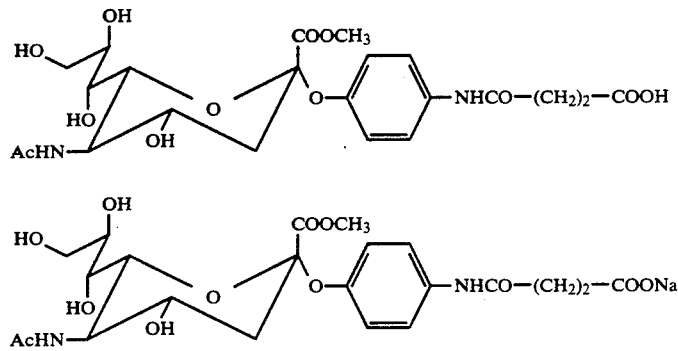

C$_{30}$H$_{38}$O$_{15}$N$_2$S
FAB-MS m/z : 699 (M$^+$ +1)
1H-NMR 500MHz (CDCl$_3$, TMS)
1.844 (3H, s, —NHCOCH$_3$),
2 019;2.038;2.059;2.127 (all 3H, all s, —OCOCH$_3$ X 4),
2.65-2.80(5H, m, —CH$_2$CH$_2$—+H$_{3eq}$),
3.585 (3H, s, 2 COOCH$_3$),
4.837 (1H, ddd, J=11.4, 10.3, 4.8 Hz, H-4),
7.414 (2H, d, J=8.4 Hz, phenyl-H),
7.534 (2H, d, J=8.4 Hz, phenyl-H),
IRνKBr/max cm$^{-1}$ 3340, 1740, 1220, Embodiment 9

Synthesis of 4'-[(methyl 5-acetamido-3, 5-dideoxy-α-D-glycero-D-galacto-2-nonulopyranosylonate)oxy] succinanilic acid and its sodium salts 222 mg of 4'-[(methyl 5-acetamido-4, 7, 8, 9-tetra-0-acetyl 3, 5 dideoxy-α-D-glycero-D-galacto 2-nonulopyranosylonate)oxy]succinanilic acid obtained in the aforementioned Embodiment 6 were dissolved in 20 ml of anhydrous methanol and 386 mg of 28% methanol solution of sodium methoxide were added at room temperature and allowed to react with stirring for two hours. Then, while cooling, 0.8 g of Dowex 50 w (H$^+$) were added and stirred to be made slightly acidic to pH 4. The ion exchange resin was removed by filtering. Solvent was removed from the filtrate liquid, and a amorphous substance was obtained. The residue obtained was purified with C$_{18}$-column chromatography (YMC.GEL ODS 60Å 60/200 mesh). The residue was eluted first with water, then with methanol, and water was added to the methanol fractional solution containing the object, freeze-dried to give 100 mg of white powdery crystals of free-acid type carboxylic acid (yield=60%, melting point=132 −135° C.). The sodium salts were similarly isolated when the amount of the aforementioned Dowex 50 w (H$^+$) was less than a half.

Physical properties of the product (COOH substance)
Element analysis C$_{22}$H$_{30}$O$_{12}$N$_2$
FAB-MS m/z : 515 (M$^+$ +1)
1H-NMR ppm/500 MHz (D$_2$O, TSP)
2.030 (1H, t, J=12.5 Hz, H$_{3ax}$),
2.039 (3H, s, —NHCOCH$_3$),
2.67-2.69(4H, m, —CH$_2$—CH$_2$—),
2.880 (1H, dd, J=12.8, 4.8 Hz, H$_{3eq}$),
7.150 (1H, d, J=8.8 Hz, phenyl-H),
7.386 (1H, d, J=8.8 Hz, phenyl-H),
IRνKBr/max cm$^{-1}$ 3400, 1730, 1660, 1550, Embodiment 10

Synthesis of [4'-(3-(N-succinimidyloxycarbonyl)propionamido) phenyl 5-acetamido-4, 7, 8, 9-tetra-O-acetyl-3, 5-dideoxy-αD-glycero D galacto 2 nonulopyranosido]onate:

100 mg of 4'-[(methyl 5-acetamido-4, 7, 8, 9-tetra-O-acetyl 3, 5-dideoxy-α-D glycero-D-galacto 2 nonulopyranosylonate)oxy]succinanilic acid obtained in the aforementioned Embodiment 6 and 38 mg of N, N'-disuccinimidyl carbonate were dissolved in 10 ml of anhydrous acetonitrile and 11.7 μl of anhydrous pyridine were added and allowed to react with stirring at room temperature.

After disappearance of raw material was confirmed with a TLC, the reaction solvent was removed under reduced pressure condition. The residue obtained was purified with silica gel column chromatography (Wakogel C=300, toluene/acetone=1/1). The residue of the obtained fractional solution was further purified with a gel filtration chromatography (LH-20, toluene/acetone =1/1) and 91 mg of white powdery crystal was obtained (yield=80%, melting point=115°-117 ° C.).

TLC: Rf=0.27 (Kieselgel 60 F$_{254}$, Merck product, toluene/acetone=1/1)

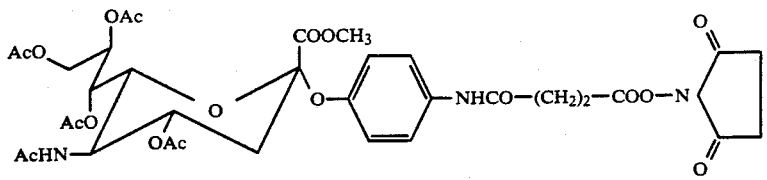

Physical properties of the product $C_{34}H_{41}O_{18}N_3$
FAB-MS m/z : 780 (M$^+$+1)
$^1$H-NMR ppm/500 MHz (CDCl$_3$, TMS)
 1.902 (3H, s, —NHCOCH$_3$),
 2.036;2.051;2.118;2.133 (all 3H, all s, —OCOCH$_3$ X 4),
 2.183 (1H, t, J=12.8 Hz, H$_{3ax}$),
 2.699 (1H, dd, J=12.8, 4.8 Hz, H$_{3eq}$),
 2.759 (2H, t, J=7.0 Hz, —CH$_2$—CH$_2$—),
 3.056 (2H, t, J=7.0 Hz, —CH$_2$ CH$_2$—),
 2.844 (4H, s, H of succinimidyl group),
 3.658 (3H, t, 2-COOCH$_3$),
 4.944 (1H, ddd, J=12.5, 10.3, 4.8 Hz, H-4),
 7.022 (2H, d, J=8 Hz, phenyl-H),
 7.413 (1H, d, J=8 Hz, phenyl-H),
IR$\nu$KBr/max cm$^{-1}$ 3360, 1740, 1670, 1540,

Embodiment 11

Synthesis of [4 succinimidophenyl 5-acetamido-4, 7, 8, 9-tetra-O-acetyl-3, 5-dideoxy-αD glycero-D-galacto-2-nonulopyranosido]onate 120 mg of 4 -[(methyl 5-acetamido-4, 7, 8, tetra O-acetyl-3, 5 dideoxy-α-D-glycero D galacto-2-nonulopyranosylonate)oxy] succinanilic acid obtained in the aforementioned Embodiment 6 and 247 mg of N, N'-disuccinimidyl carbonate and 340 mg of anhydrous pyridine were dissolved in 20 ml of anhydrous acetonitrile and allowed to react at room temperature for one day. After the reaction solvent was removed, the residue obtained was purified with silica gel column chromatography (C=300, toluene/acetone=1/1). The solvent was removed from the obtained fractional solution containing the product and white powdery crystals were obtained. The residue of the obtained fractional solution was further purified with a gel filtration chromatography (LH-20, ethyl acetate) and 24 mg of white powdery crystal was obtained (yield=20%, melting point=110°-114 ° C.).

TLC: Rf=0.35 (Kieselgel 60 F$_{254}$, Merck product, toluene/acetone=1/1)

Rf=0.26 (Kieselgel 60 F$_{254}$, Merck product, ethyl acetate)

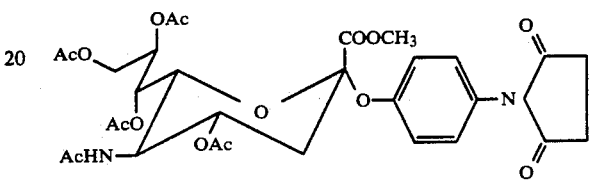

Physical properties of the product $C_{30}H_{36}O_{15}N_2$
FAB-MS m/z: 665 (M$^+$+1)
$^1$H NMR ppm/500 MHz (CDCl$_3$, TMS)
 1.913 (3H, s, —NHCOCH$_3$),
 2.047;2.049;2.121;2.153 (all 3H, all s, —OCOCH$_3$ X
 2.250 (1H, t, J=12.8 Hz, H$_{3ax}$),
 2.711 (1H, dd, J=12.8, 4.8 Hz, H$_{3eq}$),
 2.875 (4H, s, H of succinimido group),
 3.687 (3H, s, 2—COOCH$_3$),
 4.971 (1H, ddd, J=12.1, 10.6, 4.8 Hz, H-4),
 7.140 (2H, d, J=8.8 Hz, phenyl-H),
 7.203 (1H, d, J=8.8 Hz, phenyl-H),
IR$\nu$KBr/max cm$^{-1}$ 3460, 3360, 1750, 1710,

Embodiment 12

Synthesis of [4-(3-p-nitrophenyloxycarbonylpropionamide) phenyl 5 acetamido-4, 7, 8, 9-tetra-O-acetyl-3, 5-dideoxy-α-D-glycero-D-galacto-2-nonulopyranosido]onate:

52 mg of 4'-[(methyl 5-acetamido-4, 7, 8, 9-tetra 0 acetyl-3, 5-dideoxy-α-D-glycero-D-galacto-2-nonulopyranosylonato)oxy] succinanilic acid obtained in the aforementioned Embodiment 6, 24.1 mg of p-nitrophenol, and 14.5 mg of WSC (1-ethyl-3-(3-dimethylaminopropyl)-carbodiimide hydrochloride] were dissolved in 1 ml of tetrahydrofuran and allowed to react at 0 ° C. with stirring. After disappearance of raw material was confirmed with a TLC, reaction solvent was removed and the residue obtained was purified with silica gel column chromatography (Wakogel C=300, toluene/acetone=1/1) to give the fractional solution containing the object. The solvent was removed from the obtained fractional solution and 20 mg of white powdery crystals were obtained (yield=32.7 melting point=106°-108 ° C.).

TLC: Rf=0.38 (Kieselgel 60 F$_{254}$, Merck product, ethyl acetate)

Rf=0.42 (Kieselgel 60 F$_{254}$, Merck product, toluene/acetone=1/1).

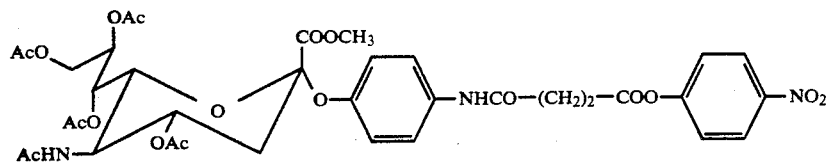

Physical properties of the product $C_{36}H_{41}O_{18}N_3$
FAB-MS m/z : 804 (M+ +1)

mg of white powdery crystals were obtained (yield=45.5%, melting point =102°–105 °C.).

TLC: Rf=0.22 (Kieselgel 60 $F_{254}$, Merck product, toluene/acetone=1/1)

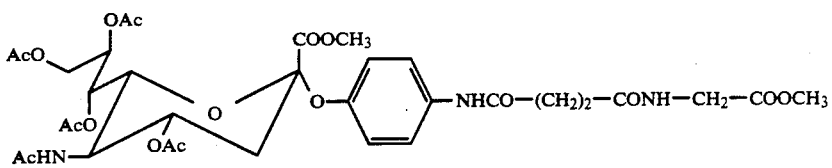

¹H NMR ppm/500 MHz (CDCl₃, TMS)
1.908 (3H, s, —NHCOCH₃),
2.038;2.047;2.126;2.132 (all 3H, all s, —OCOCH₃ X 4),
2.191 (1H, t, J=12.8 Hz, H$_{3ax}$),
2.708 (1H, dd, J=12.8, 4.4 Hz, H$_{3eq}$),
2.779 (2H, t, J=6.6 Hz, —CH₂—CH₂—),
3.019 (2H, t, J=6.6 Hz, —CH₂—CH₂—),
3.656 (3H, t, 2—COOCH₃),
4.947 (1H, ddd, J=12.1, 10.3, 4.4 Hz, H-4),
7.031 (2H, d, J=8.8 Hz, H of nitrophenyl group),
7.313 (2H, d, J=8.8 Hz, aromatic ring H of anilic acid),
7.409 (2H, d, J=8.8 Hz, aromatic ring-H of anilic acid),
8.265 (2H, d, J=8.8 Hz, nitrophenyl group).
IRνKBr/max cm⁻¹ 3350, 1740, 1660, 1520, 1340,

Embodiment 13

Synthesis of N-(4'-[(methyl 5-acetamido-4, 7, 8, 9-tetra-O-acetyl-3, 5-dideoxy-α-D-glycero-D-galacto-2-nonulopyranosylonate)oxy] succinaniloyl)glycine methyl ester [13-1] The first method (active ester process)

100 mg of 4'-[(methyl 5-acetamido-4, 7, 8, 9 tetra-O-acetyl-3, 5 dideoxy-α-D-glycero-D-galacto-2-nonulopyranosylonate) oxy] succinanilic acid obtained in the aforementioned Embodiment 6, 38 mg of N,N'-disuccinimidyl carbonate, and 11.7 μl of anhydrous pyridine were dissolved in 10 ml of anhydrous acetonitrile and allowed to react at room temperature for 2 hours. After disappearance of raw material was confirmed with a TLC, the acetontrile solution consisting of 18.4 mg of glycine methyl ester hydrochloride and 20.4 μl of triethylamine was added to the mixture of the above-mentioned active ester, and the solution was allowed to react with stirring for one day. After disappearance of the active ester with a TLC, the reaction solvent was removed and the residue obtained was purified with silica gel column chromatography (Wakogel C=300, CHCl₃/MeOH=20/1), then further with gel filtration chromatography (LH-20, MeOH) to give a fractional solution containing the product. Solvent was removed from the obtained fractional solution and 50 mg of white powdery crystals were obtained (yield=45.5%, melting point =102°–105 °C.).

TLC: Rf=0.22 (Kieselgel 60 $F_{254}$, Merck product, toluene/acetone=1/1)

Physical properties of the product $C_{33}H_{43}O_{17}N_3$
FAB MS m/z : 754 (M+ +1)
¹H-NMR ppm/500 MHz (CDCl₃, TMS)
1.898 (3H, s, —NHCOCH₃),
2.034;2.054;2.118;2.133 (all 3H, all s, —OCOCH₃ X 4),
2.175 (1H, t, J=12.5 Hz, H$_{3ax}$),
2.65°–2.71 (5H, m, —CH₂—CH₂- +H$_{3eq}$),
3.648 (3H, s, 2 —COOCH₃),
3.749 (3H, s, —NHCH₂COOCH₃),
4.946 (1H, ddd, J=12.5, 10.3, 4.8 Hz, H-4),
7.012 (2H, d, J=9.2 Hz, phenyl H),
7.417 (1H, d, J=9.2 Hz, phenyl-H),
IRνKBr/max cm⁻¹ 3300, 1750, 1660, 1550,

[13-2] The second method (mixed acid anhydride process) 107.4 mg of 4'[(methyl 5-acetamido 4, 7, 8, 9-tetra-O-acetyl-3, 5-dideoxy-α-D-glycero-D-galacto-2-nonulopyranosylonate)oxy] succinanilic acid obtained in the aforementioned Embodiment 6, and 20.4 μl of triethylamine were dissolved in 2 ml of anhydrous tetrahydrofuran, and with cooling to −12 °C. and stirring, 18.9 μl of isobutylchloroformate were added and allowed to react for 10 minutes. Then, 1 ml of anhydrous chloroform solution dissolving 18.3 mg of glycine methyl ester hydrochloride and 20.4 μl of triethylamine was added to the mixture of the above-mentioned mixed acid anhydride solution. After stirring, the solution was allowed to react at 0 °C. for 1 hour, then at room temperature with stirring for one day. After reaction solvent was removed, the residue obtained was purified with silica gel column chromatography (Wakogel C=300, CHCl₃/MeOH=20/1) to give a fractional solution containing the product. Solvent was removed from the obtained fractional solution and 36.3 mg of white powdery crystals were obtained (yield=30.6%).

TLC: Rf=0.22 (Kieselgel 60 $F_{254}$, Merck product, toluene/acetone=1/1)
Rf=0.34 (Kieselgel 60 $F_{254}$, Merck product, chloroform/methanol=20/2)

1H-NMR, IR data agreed with that obtained with the aforementioned first method (active ester process). Even when solvents used in the above-mentioned reactions (tetrahydrofuran, chloroform) were replaced with dimethylformamide, a similar product was obtained.

[13-3] The third method 37 4 mg of 4'[(methyl 5 acetamido 3, 5 dideoxy-α-D-glycero-D galacto-2-nonulopyranosylonate) oxy] succinaniloyl) glycine methyl ester and 0.8 ml of acetic anhydride were dissolved in 0.8 ml of anhydrous pyridine and allowed to react at room temperature for one day with stirring. The reaction solvent was removed and the residue obtained was purified with silica gel column chromatography (Wakogel C=300, CHCl$_1$/MeOH=20/1) to give fractional solution containing the product. Solvent was removed from the obtained fractional solution and 28.8 mg of white powdery crystals (yield=59.8%) were obtained.

TLC Rf=0.22 (Kieselgel 60 F$_{254}$, Merck product, toluene/acetone=1/1)

Rf=0.34 (Kieselgel 60 F$_{254}$, Merck product, chloroform/methanol=20/1)

1H-NM data completely agreed with that obtained with the aforementioned first method (active ester process).

Embodiment 14

Synthesis of 4'-[(methyl 5-acetamido-4, 7, 8, 9-tetra-O-acetyl-3, 5-dideoxy-α-D-glycero-D-galacto-2-nonulopyranosylonate)oxy] succinanilohylhydrazide 100 mg of 4'-[(methyl 5-acetamido-4, 7, 8, 9 tetra-O-acetyl-3, 5 dideoxy-α-D-glycero D galacto-2-nonulopyranosylonate)oxy] succinanilic acid obtained in the aforementioned Embodiment 6, 38 mg of N, N'-disuccinimidyl carbonate, and 11.7 μl of anhydrous pyridine were dissolved in 10 ml of anhydrous acetonitrile and allowed to react at room temperature for 8 hours. After disappearance of raw material was confirmed with a TLC, while cooling, 10 μl of anhydrous hydrazine was added and allowed to react for one day. The reaction solvent was removed and the residue obtained was purified with gel filtration chromatography (LH-20, MeOH), then further with silica gel chromatography (Wakogel C-300, CHCl$_1$/MeOH=10/1) to give a fractional solution containing the product. Solvent was removed from the obtained fractional solution and 40.5 mg of white powdery crystal (yield=40%, melting point=110°-113 ° C.) were obtained.

Rf=0.52 (Kieselgel 60 F$_{254}$, Merck product, ethyl acetate/methanol=5/3)

Rf=0.20 (Kieselgel 60 F$_{254}$, Merck product, chloroform/methanol=10/1)

1.811 (3H, s, —NHCOCH$_3$),
1.972;2.031;2.055 (6H;3H;3H, all s, —OCOCH$_3$ X 4),
2.108 (1H, t, J=12.5 Hz, H$_{3ax}$),
2.492 (4H, m, —CH$_2$—CH$_2$—),
2.622 (3H, m, —CH$_2$—CH$_2$— +H$_{3eq}$),
3.544 (3H, s, 2 —COOCH$_3$),
4.876 (1H, m, H-4),
6.921 (2H, d, J=8.8 Hz, phenyl-H),
7.355 (2H, d, J=8.8 Hz, phenyl-H),
IVνKBr/max cm$^{-1}$ 3300, 1740, 1660, 1540,

Embodiment 15

Synthesis of N-4'-[methyl (5-acetamido-3,5-dideoxy-α-D-glycero-D-galacto 2 nonulopyranosylonate)oxy] succinaniloyl) glycine methyl ester 98 mg of 4,-[(methyl 5-acetamido 3, 5 dideoxy-α-D glycero-D-galacto-2-nonulopyranosylonate)oxy] succinanilic acid obtained in the aforementioned Embodiment 9 and 27.1 μl of triethylamine were dissolved in 1 ml of anhydrous dimethylformamide and 25 ml of isobutylchloroformate were added with stirring and cooling ( 15 ° C.), then allowed to react for 10 minutes. Then, 1 ml of anhydrous dimethylformamide solution dissolving 24.4 mg of glycine methyl ester hydrochloride salt and 27.1 μl of triethylamine was added to the above-mentioned acid anhydride solution. After stirring, the solution was allowed to react at 0 ° C. for 1 hour, then at room temperature with stirring for one day. After the reaction solvent was removed under reduced pressure conditions, the residue obrtained was purified with C$_{18}$-column chromatography (YMC.GEL ODS 60 Å 60/200 mesh). The solution was eluted first with water, then with water/methanol=1/1 solution, and the fractional solution containing the product was freeze-dryed to give 50 mg of white powdery crystals (yield=45%, melting point=111°-113 ° C.).

TLC: Rf=0.46 (Kieselgel 60 F$_{254}$, Merck product, CHCl$_3$/MeOH/ACOH=6/3/0.5)

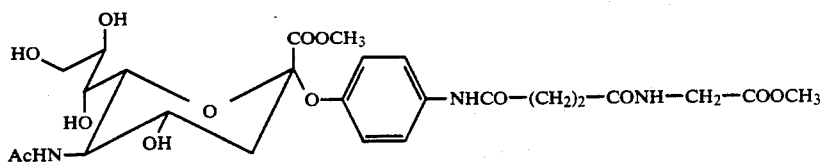

Physical properties of the product

C$_{25}$H$_{35}$O$_{13}$N$_3$
FAB MS m/z : 586 (M$^+$+1)
1H-NMR ppm/500 MHz (D20, TSP)
2.040 (1H, t, J=12.5 Hz, H$_{3ax}$),

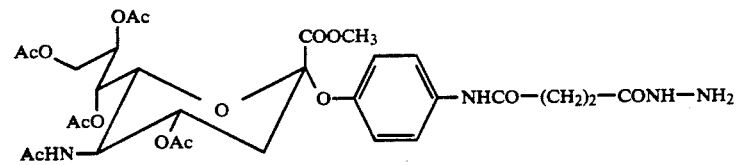

Physical properties of the product

Element analysis C$_{30}$H$_{40}$O$_{15}$N$_4$
FAB-MS m/z: 697 (M$^+$+1)
1H-NMR ppm/500 MHz (CDCl$_3$, TMS)

2.051 (3H, s, —NHCOCH$_3$),
2.68-2.74 (4H m —CH$_2$—CH$_2$—)
2.890 (1H, dd, J=12.8, 4.4 Hz, H$_{3eq}$),
3.726 (3H, s, 2—COOCH$_3$),
3.763 (3H, s, —NHCH$_2$COOCH$_3$), 7.164 H, d, J=8.8 Hz, phenyl-H),
7.397 (2H, d, J=8.8 Hz, phenyl H),
IRνKBr/max cm⁻¹ 3350, 1740, 1650, 1550, Embodiment 16

Synthesis of N 4'-[methyl (5-acetamido-4, 7, 8, 9-tetra-O-acetyl-3, 5-dideoxy-α-D-glycero-D-galacto-2-nonulopyranosylonate)oxy] succinaniloyl) glycine 100 mg of 4'-[(methyl 5-acetamido-4, 7, 8, 9-tetra-O-acetyl-3, 5-dideoxy-α-D-glycero-D-galacto-2-nonulopyranosylonate) oxy] succinanilic acid obtained in the aforementioned Embodiment 6 and 20.4 μl of triethylamine were dissolved in 2 ml of anhydrous tetrahydrofuran, and 18.9 μl of isobutylchloroformate were added with stirring and cooling (−15 °C.), then allowed to react for 10 minutes. Then, the above mentioned acid anhydride solution was added to 1 ml of tetrahydrofuran-water (1:1) solution dissolving 11 mg of glycine and 0.4 μl of triethylamine with cooling (0 °C.) and stirring. The solution was allowed to react at 0 °C. for hour, then at room temperature with stirring for one day. After the reaction solvent was removed under reduced pressure conditions, the residue obtained was freeze-dried. The methanol solution of the residue obtained was made acidic with Dowex 50 w (H+), then solvent was removed.

The residue was purified with silica gel column chromatography (Wakogel C 300, acetate/methanol=5/3) to give the fractional solution containing the product. Solvent was removed from the fractional solution and 54 mg of white powdery crystals were obtained (yield=50%, melting point=105°–108 °C.).

TLC: Rf=0.15 (Kieselgel 60 F₂₅₄, Merck product, acetate/methanol=5/3)

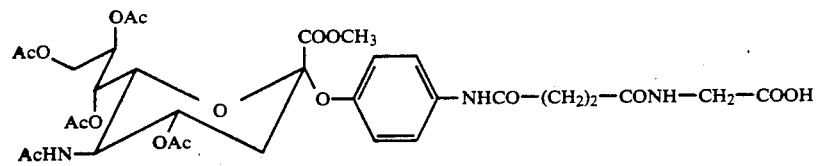

Physical properties of the product $C_{32}H_{41}O_{17}N_3$
FAB-MS m/z 740 (M+ +1)
¹H-NMR ppm/500 MHz (CDCl₃, TMS)
1.880 (3H, s, —NHCOCH₃),
024;2.085;2.117 (all s, —OCOCH₃ X 4),
3.605 (3H, s, 2—COOCH₃),
3.61 (2H, broad s, -NH-CH₂—COOH),
4.93 (1H, m, H 4),
6.962 (2H, d, J=8.1 Hz, phenyl H),
7.412 (2H, d, J=8.1 Hz, phenyl-H),
IRνKBr/max cm⁻¹ 3350, 1740, 1660, 1540,
What is claimed is:

1. A sialic acid derivative with active ester groups, having the formula:

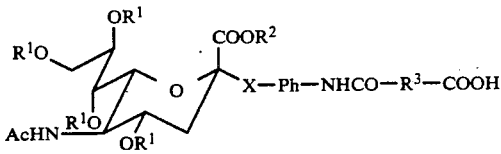

wherein $R^1$ is hydrogen or acetyl; $R^2$ is hydrogen or lower alkyl; $R^3$ is $C_2H_4$, $C_3H_6$ or $C_2H_2$; Ac is acetyl; Ph is phenyl; and X is oxygen or sulfur.

2. The sialic acid derivative of claim 1, wherein $R^3$ is $C_2H_4$.

3. The sialic acid derivative of claim 1, wherein $R^3$ is $C_3H_6$.

4. The sialic acid derivative of claim 1, wherein $R^3$ is $C_2H_2$.

5. A sialic acid derivative with active ester groups, having the formula:

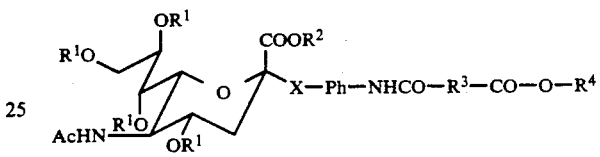

wherein $R^1$ is hydrogen or acetyl; $R^2$ is hydrogen or lower alkyl; $R^3$ is $C_2H_4$, $C_3H_6$ or $C_2H_2$; $R^4$ is the residue left after removing an hydroxyl group from a specie selected from the group consisting of N-hydroxysuccinimide, N-hydroxy-5-norbornene-2,3-dicarboximide, N-hydroxyphthalimide, Nhydroxybenzotriazole, p-nitrophenol, 2,4-dinitrophenol, 2,4,5-trichlorophenol and pentachlorophenol; Ac is acetyl; Ph is phenyl; and X is oxygen or sulfur.

6. The sialic acid derivative of claim 5, wherein $R^3$ is $C_2H_4$.

7. The sialic acid derivative of claim 5, wherein $R^3$ is $C_3H_6$.

8. The sialic acid derivative of claim 5, wherein $R^3$ is $C_2H_2$.

9. A sialic acid derivative with active ester groups, having the formula:

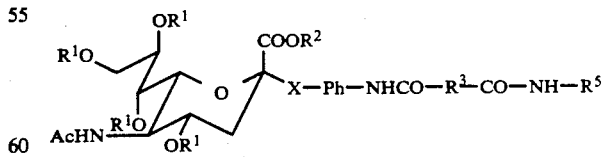

wherein $R^1$ is hydrogen or acetyl; $R^2$ is hydrogen or lower alkyl; $R^3$ is $C_2H_4$, $C_3H_6$ or $C_2H_2$; $R^5$ isamino or, —(CH₂)$_m$—COOR⁶, wherein m=1–4 and $R^6$ is hydrogen or C₁₋₄alkyl; Ac is acetyl; Ph is phenyl; and X is oxygen or sulfur.

10. The sialic acid derivative of claim 9, wherein $R^3$ is $C_2H_4$.

11. The sialic acid derivative of claim 9, wherein $R^3$ is $C_3H_6$.

12. The sialic acid derivative of claim 9, wherein $R^3$ is $C_2H_2$.

13. The sialic acid derivative of claim 9, wherein $R^5$ is amino.

14. The sialic acid derivative of claim 9, wherein $R^5$ is $-(CH_2)_m-COOR^6$.

15. A sialic acid derivative having the formula:

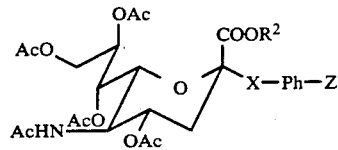

wherein $R^2$ is hydrogen or lower alkyl, Ac is acetyl, Ph is phenyl, X is oxygen or sulfur, and Z is a specie selected from the group consisting of an amino group, N,N'-dialkyl-substituted amino group, and an N-succinimide group.

16. The sialic acid derivative of claim 15, wherien Z is an amino group.

17. The sialic acid derivative of claim 15, wherein Z is selected from the group consisting of an amino group and an N,N'-dialkyl-substituted amino group.

18. The sialic acid derivative of claim 15, wherein Z is selected from the group consisting of an amino group and an N-succinimide group.

* * * * *

UNITED STATES PATENT AND TRADEMARK OFFICE
CERTIFICATE OF CORRECTION

PATENT NO. : 5,077,397
DATED : December 31, 1991
INVENTOR(S) : Yoshimura et al

It is certified that error appears in the above-identified patent and that said Letters Patent is hereby corrected as shown below:

At column 1, line 42, change "in" to -- is --.

At column 2, line 23, delete "r".

At column 2, line 41, change "a" to -- an --.

At column 3, line 38, after "$R^2$" insert -- is --.

At column 3, line 40, change "is a" to -- is an --.

At column 3, line 40, after "Ph" insert -- is a --.

At column 4, line 66, delete "the".

At column 4, line 67, after "give" insert -- the following --.

At column 4, line 68, delete "substance".

At column 5, line 48, change "$CHCl_3MeOH$" to -- $CHCl_3$/MeOH --.

At column 5, line 67, change "$^1$H-N" to -- $^1$H-NMR ppm/500MHz --.

At column 5, line 68, change "1 932" to -- 1.932 --; change " -$NHCOCH_3$" to -- -NHCO$\underline{CH}_3$ --.

At column 6, line 5, change "2'COO$\underline{CH}_3$" to -- 2-COO$\underline{CH}_3$ --.

At column 6, line 7, after "phenyl-H)" insert -- , --.

At column 6, line 9, change "maxcm$^{-1}$" to -- max cm$^{-1}$ --.

UNITED STATES PATENT AND TRADEMARK OFFICE
CERTIFICATE OF CORRECTION

PATENT NO. : 5,077,397

DATED : December 31, 1991

INVENTOR(S) : Yoshimura et al

It is certified that error appears in the above-identified patent and that said Letters Patent is hereby corrected as shown below:

At column 6, line 22, change "galacto-1" to -- galacto-2 --.

At column 6, line 62, change "V 6 87" to -- 6.87 --.

At column 7, line 28, change "pp/m500" to -- ppm/500 --.

At column 8, line 43, change "100° 14 102°C" to -- 100-102°C --.

At column 8, line 59, change "1H" to -- $^1$H --.

At column 8, line 65, after COOCH$_3$), insert
-- 4.833 (1H, ddd, J=11.7, 10.3, 4.8Hz, H-4), --.

At column 8, line 66, change "603" to -- 6.603 --.

At column 8, line 67, change "266" to -- 7.266 --.

At column 8, line 68, after "cm$^{-1}$" insert -- : --.

At column 9, line 30, after "TLC" insert -- : --.

At column 9, line 47, change "H" to -- $^1$H --.

At column 9, line 54, change "-COOCH$_3$" to -- -COO$\underline{CH}_3$ --.

At column 9, line 58, after "cm$^{-1}$" insert -- : --.

At column 10, line 28, change "-OCOCH$_3$X" to -- -OCOCH$_3$X4), --.

UNITED STATES PATENT AND TRADEMARK OFFICE
CERTIFICATE OF CORRECTION

PATENT NO. : 5,077,397
DATED : December 31, 1991
INVENTOR(S) : Yoshimura et al

It is certified that error appears in the above-identified patent and that said Letters Patent is hereby corrected as shown below:

At column 10, line 32, change "H 4" to -- H-4 --.

At column 10, line 33, change "olefin H" to -- olefin-H --.

At column 10, line 43, change "olefin H" to -- olefin-H --.

At column 10, line 46, after "$cm^{-1}$" insert -- : --.

At column 10, line 54, change "8," to --8, 9--.

At column 10, lines 67 to 68, change "11-9·" to -- 119 --.

At column 11, line 34, change "1H" to -- $^1H$ --.

At column 11, line 36, change "2 019" to -- 2.019 --.

At column 11, line 39, change "2 $COOCH_3$" to -- 2-$COOCH_3$ --.

At column 11, line 44, after "$cm^{-1}$" insert -- : --.

At column 11, line 59, change "a" to -- an --.

At column 12, line 34, change "1H" to -- $^1H$ --.

At column 12, between lines 39 and 40,
    insert -- 3.748 (3H, s, 2-$COOCH_3$), --.

At column 12, line 41, after "$cm^{-1}$" insert -- : --.

At column 12, line 60, delete "condition".

UNITED STATES PATENT AND TRADEMARK OFFICE
CERTIFICATE OF CORRECTION

PATENT NO. : 5,077,397

DATED : December 31, 1991

INVENTOR(S) : Yoshimura et al

It is certified that error appears in the above-identified patent and that said Letters Patent is hereby corrected as shown below:

column 12, line 63, delete "a".

column 12, line 65, change "crystal was" to -- crystals were --.

column 13, line 42, after "cm$^{-1}$" insert -- : --.

column 13, line 44, change "4 succinimidophenyl" to -- 4-succinimidophenyl --.

column 13, line 46, change "onate" to -- onate: --.

column 13, line 47, change "4-[" to -- 4'-[ --.

column 13, line 47, change "8, tetra" to -- 8, 9 tetra --.

column 14, line 30, change "$^1$H NMR" to -- $^1$H-NMR --.

column 14, line 32, change "-OCOCH$_3$ X" to -- -OCO$\underline{CH}_3$ X4 --.

column 14, line 40, after "cm$^{-1}$" insert -- : --.

column 14, line 63, change "32.7" to -- 32.7% --.

column 15, line 23, change "$^1$H NMR" to -- $^1$H-NMR --.

column 15, line 39, after "cm$^{-1}$" insert -- : --.

column 15, line 46, change "ester [13-1]" to -- ester: [13-1] --.

UNITED STATES PATENT AND TRADEMARK OFFICE
CERTIFICATE OF CORRECTION

PATENT NO. : 5,077,397
DATED : December 31, 1991
INVENTOR(S) : Yoshimura et al

It is certified that error appears in the above-identified patent and that said Letters Patent is hereby corrected as shown below:

At column 16, line 31, change "2.65·" to -- 2.65 --.

At column 16, line 37, after "$cm^{-1}$" insert -- : --.

At column 17, line 1, change "37 4 mg of 4'[" to -- 37.4 mg of 4'-[ --.

At column 17, line 9, change "$CHCl_1$" to -- $CHCl_3$ --.

At column 17, line 13, change "TLC Rf" to -- TLC:Rf --.

At column 17, line 17, change "-NM" to -- -NMR --.

At column 17, line 24, change "succinanilohylhydrazide" to -- succinanilohylhydrazide: --.

At column 17, line 38, change "$CHCl_1$" to -- $CHCl_3$ --.

At column 18, line 4, change "$\underline{CH_2}$-$\underline{CH_2}$" to -- $\underline{CH_2}$-$CH_2$ --.

At column 18, line 5, change "$\underline{CH_2}$-$\underline{CH_2}$" to -- $CH_2$-$\underline{CH_2}$ --.

At column 18, line 10, change "IV" to -- IR --.

At column 18, line 10, after "$cm^{-1}$" insert -- : --.

At column 18, line 16, change "ester" to -- ester: --.

At column 18, line 18, change "4," to -- 4' --.

UNITED STATES PATENT AND TRADEMARK OFFICE
CERTIFICATE OF CORRECTION

PATENT NO. : 5,077,397
DATED : December 31, 1991
INVENTOR(S) : Yoshimura et al

It is certified that error appears in the above-identified patent and that said Letters Patent is hereby corrected as shown below:

At column 18, line 23, change "15" to -- -15 --.

At column 18, line 31, change "obrtained" to -- obtained --.

At column 19, line 3, after "cm$^{-1}$" insert -- : --.

At column 19, line 9, change "glycine" to -- glycine: --.

At column 19, line 20, change "0.4" to -- 20.4 --.

At column 19, line 22, change "for hour" to -- for 1 hour --.

At column 19, line 29, change "C 300" to -- C-300 --.

At column 19, line 56, change "m/z" to -- m/z: --.

At column 19, line 59, change "024" to -- 2.024 --.

At column 19, line 62, change "H 4" to -- H-4 --.

At column 19, line 63, change "phenyl H" to -- phenyl-H --.

At column 19, line 65, after "cm$^{-1}$" insert -- : --.

At column 20, line 33, change "Nhydroxybenzotriazole," to -- N-hydroxybenzotriazole, --.

At column 20, line 63, change "isamino" to -- is amino --.

UNITED STATES PATENT AND TRADEMARK OFFICE
CERTIFICATE OF CORRECTION

PATENT NO. : 5,077,397
DATED : December 31, 1991
INVENTOR(S) : Yoshimura et al

It is certified that error appears in the above-identified patent and that said Letters Patent is hereby corrected as shown below:

At column 22, line 14, change "wherien" to -- wherein --.

Signed and Sealed this

Ninth Day of November, 1993

Attest:

BRUCE LEHMAN

Attesting Officer

Commissioner of Patents and Trademarks